(12) United States Patent
Parzy et al.

(10) Patent No.: US 9,028,418 B2
(45) Date of Patent: May 12, 2015

(54) MEASUREMENT OF SYSTOLIC PRESSURE

(75) Inventors: Denis Parzy, Saint Didier au Mont d'Or (FR); Benoit Guibert, Seyssuel (FR)

(73) Assignee: ATYS SARL, Soucieu en Jarrest (FR)

( * ) Notice: Subject to any disclaimer, the term of this patent is extended or adjusted under 35 U.S.C. 154(b) by 333 days.

(21) Appl. No.: 13/131,768

(22) PCT Filed: Dec. 3, 2009

(86) PCT No.: PCT/FR2009/052407
§ 371 (c)(1),
(2), (4) Date: Jul. 26, 2011

(87) PCT Pub. No.: WO2010/063976
PCT Pub. Date: Jun. 10, 2010

(65) Prior Publication Data
US 2011/0282219 A1    Nov. 17, 2011

(30) Foreign Application Priority Data
Dec. 5, 2008 (FR) ...................... 08 58291

(51) Int. Cl.
*A61B 5/02* (2006.01)
*A61B 5/022* (2006.01)
*A61B 5/0225* (2006.01)
*A61B 5/021* (2006.01)

(52) U.S. Cl.
CPC ............. *A61B 5/02241* (2013.01); *A61B 5/021* (2013.01); *A61B 5/022* (2013.01); *A61B 5/02141* (2013.01); *A61B 5/02225* (2013.01); *A61B 5/02255* (2013.01)

(58) Field of Classification Search
USPC .................................................. 600/481–507
See application file for complete search history.

(56) References Cited

U.S. PATENT DOCUMENTS

| 6,400,971 B1 | 6/2002 | Finarov et al. | |
| 2005/0148885 A1 * | 7/2005 | Tweed et al. | 600/490 |
| 2006/0074322 A1 * | 4/2006 | Nitzan | 600/485 |
| 2008/0077024 A1 | 3/2008 | Schnall | |

FOREIGN PATENT DOCUMENTS

WO    WO 2007/097702    *   8/2007

* cited by examiner

*Primary Examiner* — Michael D'Angelo
(74) *Attorney, Agent, or Firm* — Ladas & Parry LLP

(57) ABSTRACT

A noninvasive method for measuring systolic blood pressure $P_{syst}$, by applying and maintaining an astringent emptying pressure P1, which is above the systolic blood pressure $P_{syst}$, on a first zone of the finger located in the vicinity of the distal part of the finger, applying and maintaining an astringent occluding pressure P2, which is above the systolic blood pressure $P_{syst}$, on a second zone of the finger located upstream of the first zone, releasing the emptying pressure P1, releasing the occluding pressure P2 in a controlled manner, and, at the same time, acquiring at least the occluding pressure P2 and at least the blood volume $V_s$, at the level of the first zone as a function of time, and calculating the systolic blood pressure $P_{syst}$ corresponding to the occluding pressure P2 at the moment of blood return in the finger, characterized by a substantially positive variation in the blood volume $V_s$ of the finger at the level of the first zone.

18 Claims, 4 Drawing Sheets

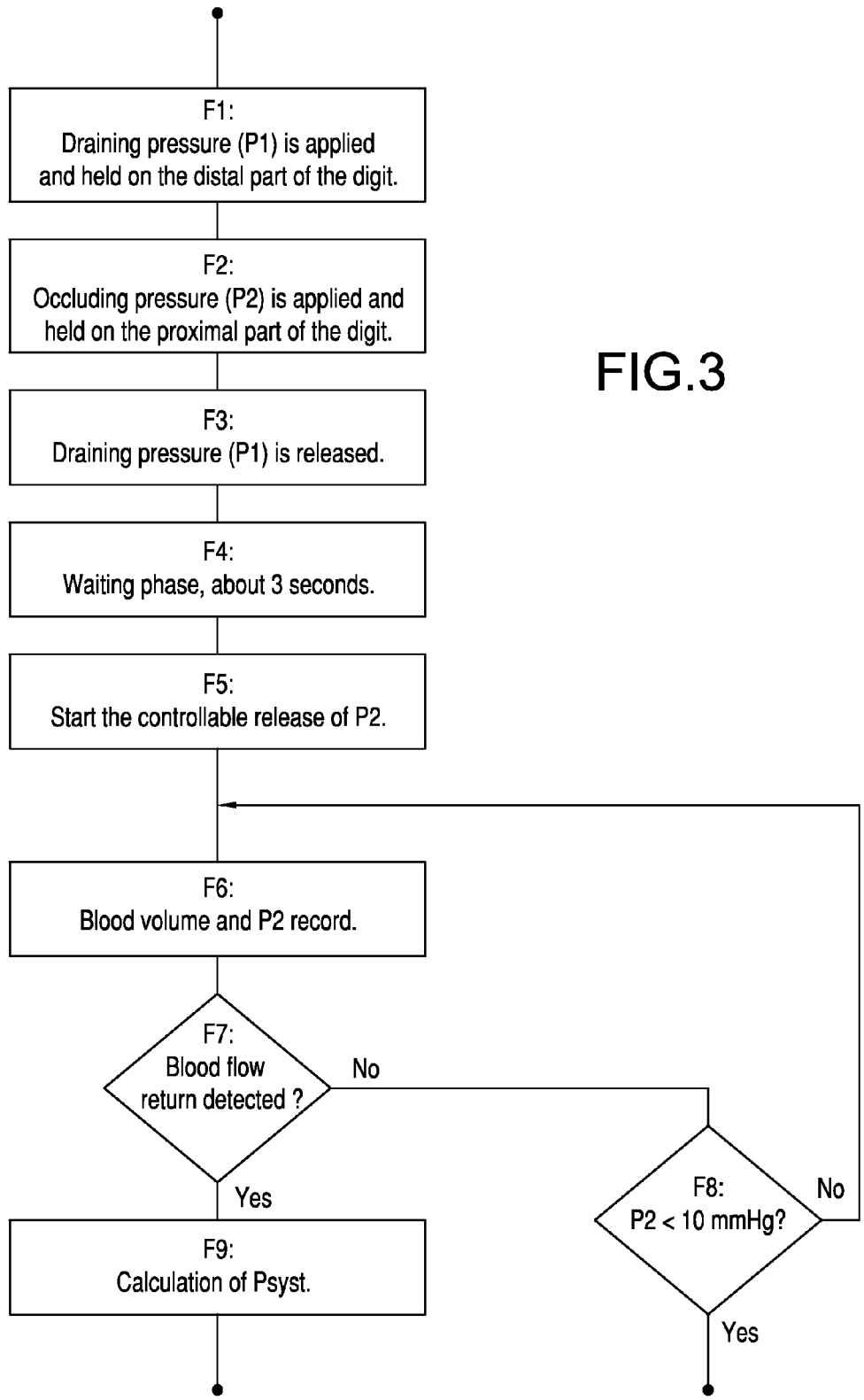

MEASUREMENT OF SYSTOLIC PRESSURE

The present invention concerns the general technical field of non-invasive blood pressure measuring apparatus.

More particularly, the present invention concerns the field of finger and in particular toe devices for measuring systolic blood pressure.

Patent EP 1 217 941 describes an optical device used to measure different blood parameters, non-invasively and using a finger holder. The finger holder comprises a first element, adapted to be held on a finger and equipped with a measuring unit, and a second element positioned upstream of the first element and equipped with an occluding member. The occluding member, before taking a measurement, applies a pressure greater than the patient's systolic blood pressure so as to create blood flow cessation in the finger. The measuring unit then continuously determines the absorbency of the finger at different wavelengths.

Systolic blood pressure can be determined with this kind of device by progressively releasing the pressure applied by the occluding member until the measuring unit detects a variation in absorbency of the finger, characterized by a return to pulsatile arterial flow.

However, when the patient's systolic blood pressure is low, for example lower than 30 mmHg, the arterial blood flow is little pulsatile. On this account, the detection of return to arterial pulsatility is imprecise and the same applies to the measurement of systolic blood pressure. Therefore this type of device is not adapted for measuring low systolic blood pressures.

Similarly, patent application US 2005/148885 describes a quasi-continuous non-invasive device for measuring a person's arterial blood pressure. This device comprises an inflatable finger cuff provided with a photo-plethysmograph sensor measuring the finger's blood pressure. The inflating/deflating of the cuff is conducted so as to maintain the sensor applied to the finger. Said measuring device, during inflation and deflation of the cuff, uses data on the variable component of the sensor to track and monitor the mean blood pressure. During deflation, this device does not use data from the sensor's signal to determine precisely the value of systolic pressure.

It is one objective of the invention to overcome the disadvantages of the state of the art by allowing precise measurement of low systolic blood pressures.

A further objective of the invention is to propose a non-invasive measuring method allowing precise finger and particularly toe measurement of low systolic blood pressures.

For this purpose a non-invasive method for measuring systolic blood pressure according to the invention comprises the following steps:
- applying and maintaining an astringent draining pressure on a first region located in the vicinity of the distal part of the finger/toe,
- applying and maintaining an astringent occluding pressure, that is greater than the systolic blood pressure of the finger/toe, to a second region of the finger/toe located upstream of the first region,
- releasing the draining pressure,
- releasing the occluding pressure in controlled manner and at the same time acquiring at least the occluding pressure and at least the blood volume in the finger/toe at the first region as a function of time,
- calculating the systolic blood pressure corresponding to the occluding pressure at the time of blood return in the finger/toe characterized by a substantially positive variation in the blood volume of the finger/toe at the first region.

According to one preferred characteristic of embodiment, the draining pressure is greater than the systolic blood pressure in the finger/toe.

Advantageously by draining the finger/toe before measurement, it is possible to increase the blood flow at the time of blood return by superimposing the contributions made by arterial flow, microcirculation and non-pulsatile flow towards filling, which facilitates evidencing thereof.

Also, a measuring method according to the invention may additionally have at least one the following additional characteristics:
- the draining and occluding pressures are applied and released automatically,
- the draining pressure is applied and released manually whilst the occluding pressure is applied and released automatically,
- the method comprises a waiting phase lasting a time of between 0 and 5 s preferably of the order of 3 s, occurring after release of the draining pressure,
- the calculation step of systolic blood pressure comprises extracting a pulsatile component representing the pulsatile arterial flow in the finger/toe based on the variation in blood volume of the finger/toe at the first region as a function of time, then calculating the systolic blood pressure by determining the occluding pressure at the time when the pulsatile component of the signal returns,
- the calculating step of systolic blood pressure consists of extracting a non-pulsatile component representing filling of the finger/toe resulting from pulsatile arterial flow, from microcirculation and/or from non-pulsatile arterial flow, based on the variation in blood volume of the finger/toe at the first region as a function of time, then of calculating the systolic blood pressure by determining the occluding pressure at the time when the non-pulsatile component varies substantially positively,
- the method consists of adjusting the time required for release of occluding pressure so that it occurs over a fixed number of cardiac cycles.

A further objective of the invention is to propose a measuring device allowing precise finger and in particular toe measurement of low systolic blood pressures.

For this purpose, a non-invasive device according to the invention for measuring the systolic blood pressure of a finger/toe having a distal part comprises a first element comprising a sensor capable of measuring the blood volume of the finger/toe at a first region located in the vicinity of the distal part of the finger/toe, and a draining member capable of applying or transmitting a draining pressure to the first region of the finger/toe, a second element comprising an arterial occluding member capable of applying and/or of maintaining an occluding pressure on a second region of the finger/toe upstream of the first region, and an inflating and deflating device servo-controlled by control electronics ensuring inflation and deflation of at least the arterial occluding member.

Also, a measuring device according to the invention may additionally have one of the following additional characteristics:
- the servo-controlled inflating and deflating device also ensures the inflation and deflation of the draining member,
- at least the occluding member is formed of an air chamber, the device comprises a pressure measurement system measuring at least the pressure applied by the arterial occluding member, and preferably also the pressure applied by the draining member, the device comprises a processing system controlled by the control electronics and comprising an acquisition stage which acquires at least the data delivered by the pressure measurement system and by the sensor, and a processing unit comprising means for determining the time when the blood volume of the finger/toe at the first region varies substantially positively, and means for calculating systolic blood pressure corresponding to the occluding pressure at the time when the blood volume in the finger/toe at the first region varies substantially positively, the processing unit further comprises means for extracting a pulsatile component representing pulsatile arterial flow in the finger/toe at the first region as a function of time, means for determining the moment when the pulsatile component of the signal returns, and means for calculating systolic blood pressure corresponding to the occluding pressure at the time when the pulsatile component of the signal returns, the processing unit comprises means for extracting a non-pulsatile component representing filling of the finger/toe resulting from pulsatile arterial flow, from microcirculation and/or from non-pulsatile arterial flow as a function of time, means for determining the time when the non-pulsatile component varies substantially positively, and means for calculating systolic blood pressure corresponding to the occluding pressure at the time when the non-pulsatile component varies substantially positively, the processing unit comprises comparison means between the value of the occluding pressure and the value of the minimum systolic blood pressure which can be measured by the device, for example 10 mmHg, the control electronics drive the inflating and deflating device to apply the draining pressure before application of the occluding pressure, and to release the draining pressure after application of the occluding pressure and before controlled release of the occluding pressure, the control electronics drive the acquisition stage so that, during controlled release of the occluding pressure, it acquires at least the data delivered by the pressure measurement system and by the sensor, the control electronics drive the processing unit to calculate systolic pressure during controlled release of the occluding pressure and at the time of detection of blood return to the finger/toe.

Various other characteristics will become apparent from the description below given with reference to the appended drawings which, as non-limiting examples, illustrate embodiments of the subject of the invention.

FIG. 1 schematically illustrates a device according to the invention.

FIG. 2 schematically illustrates an example of embodiment of the servo-controlled inflating and deflating device.

FIG. 3 is a logical diagram of the method of the invention.

Figure 1:
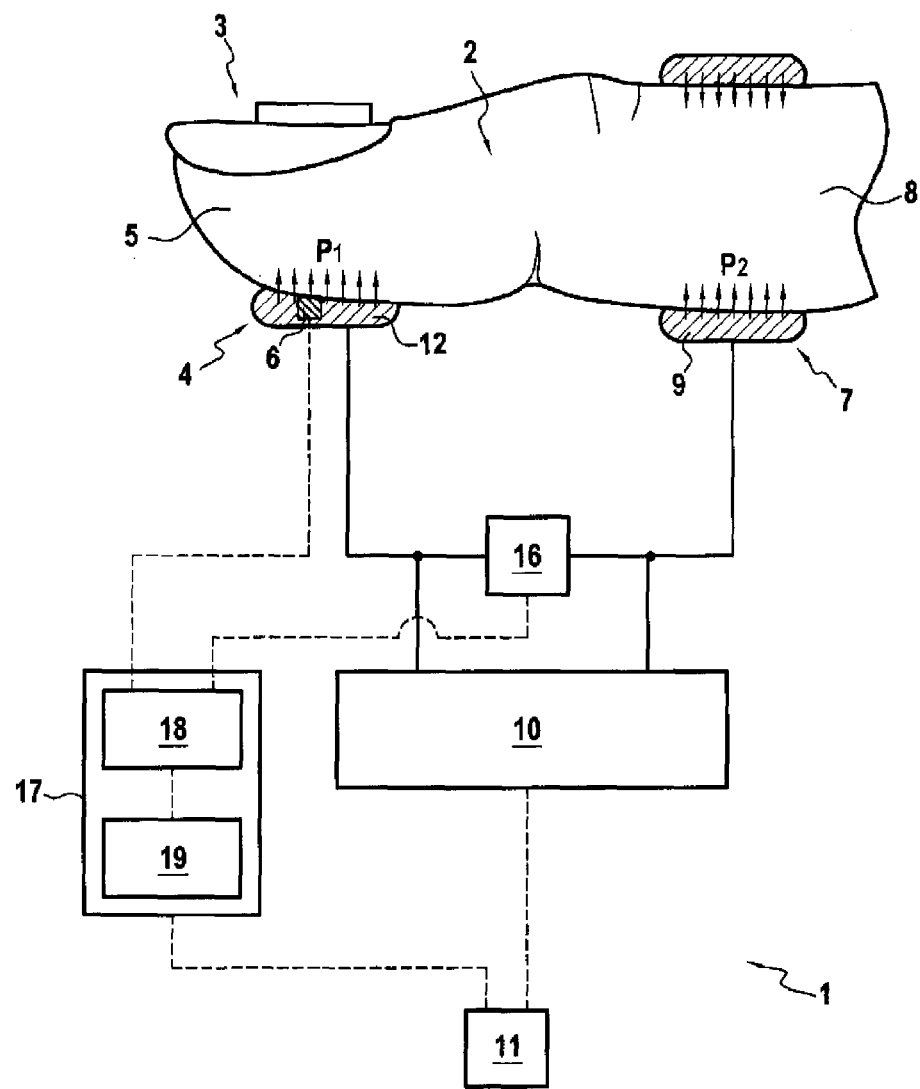

FIG. 1 shows an example of embodiment of a non-invasive device 1 for measuring a patient's systolic blood pressure. The device 1 is intended to be placed on a finger/toe 2 having a distal part 3.

The measuring device 1 may optionally be placed on a patient's finger or advantageously on a toe.

The device 1 comprises a first element 4 which can be positioned at a first region 5 of the finger/toe 2 located in the vicinity of the distal part 3. The first element 4 comprises a sensor 6 capable of measuring the blood volume of the finger/toe 2 at the first region 5. The sensor 6 may be of photoplethysmograph type, ultrasound Doppler or LASER Doppler.

The device 1 also comprises a second element 7 which can be positioned at a second region 8 of the finger/toe 2 located upstream of the first region 5. The second element 7 comprises an arterial occluding member 9 capable of applying and/or maintaining a variable, astringent occluding pressure P2 at the second region 8 of the finger/toe 2. At its maximum value, the occluding pressure P2 is higher than the patient's systolic blood pressure $P_{syst}$ so that it is possible to block the blood flow in that part of the finger/toe 2 located downstream of the second region 8.

The occluding member 9 can be formed of any suitable means, for example a pneumatic device and preferably in the form of an air chamber surrounding the finger/toe 2. Advantageously, the air chamber allows uniform distribution of the occluding pressure P2 to be obtained, and its bracelet-shape enables maintaining thereof around the finger/toe 2.

The deflation and deflation of the arterial occluding member 9 are achieved by means of a servo-controlled inflating and deflating device 10 controlled by control electronics 11.

According to the invention, the first element 4 also comprises a draining member 12 capable of applying, of maintaining and/or transmitting a draining pressure P1 to the first region 5 of the finger/toe 2. The draining pressure P1 is higher than the patient's systolic blood pressure $P_{syst}$ so that it is possible substantially to drain the distal part 3 of the blood contained therein.

Figure 2:
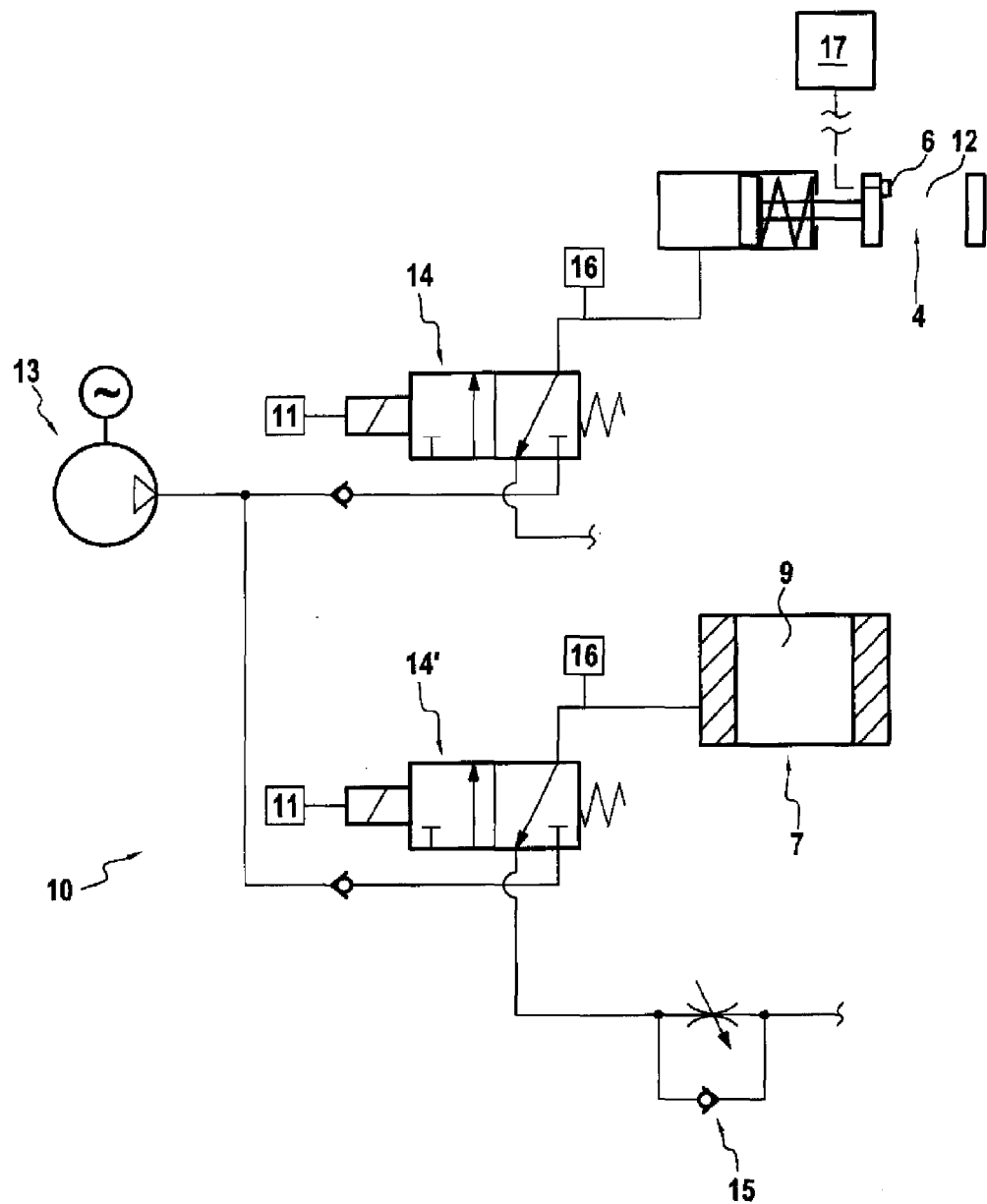

The draining member 12 can be formed of any suitable means and preferably of a pneumatic device such as an air chamber or, as illustrated FIG. 2, of a cylinder whose piston is mobile in translation as far as an abutment. If the device is pneumatic, the inflating and deflating of the draining member 12 are preferably carried out by the servo-controlled inflating and deflating device 10. Advantageously, the draining member 12 is formed so that it can be maintained on the finger/toe 2, for example in the form of a bracelet or clip.

In one variant of the invention, not illustrated, the draining pressure P1 is applied and released manually at the first region 5.

FIG. 2 schematically illustrates an example of embodiment of the servo-controlled inflation and deflation device 10. In this example, the device 10 is capable of simultaneously ensuring the inflation and deflation of the occluding member 9 and of the draining member 12.

The inflation device 10 is composed of air supply means for example a pump which supplies two pneumatic distributors 14, 14' driven by the control electronics 11 and respectively connected to the occluding member 9 and to the draining member 12. In its discharge position, the distributor 14' connects the occluding member 9 with flow reducing means 15, for example and as in the illustrated example a flow restrictor.

According to the illustrated example of embodiment, the measuring device 1 also comprises a pressure measurement system 16 adapted for measuring at least the occluding pressure P2 applied by the arterial occluding member 9. In this example, the pressure measurement system 16 is also adapted for measuring the draining pressure P1 applied by the draining member 12.

The measurement device 1 further comprises a processing system 17 controlled by control electronics 11. The processing system 17 comprises an acquisition stage 18 which acquires at least the blood volume value $V_s$ in the finger/toe 2 over time delivered by the sensor 6, and the occluding pressure value P2 over time delivered by the pressure measurement system 16. The processing system 17 also comprises a processing unit 19 which calculates the systolic blood pressure $P_{syst}$.

The measurement device 1 is used according to the method of the invention whose logical diagram is shown FIG. 3, to allow measurement of a patient's systolic pressure $P_{syst}$.

At the first phase F1 of the method, the draining pressure P1 is applied and held for example by means of the draining member 12 at the first region 5 located in the vicinity of the distal part 3 of the finger/toe. The draining pressure P1 is greater than the systolic blood pressure $P_{syst}$ so as substantially to drain the finger/toe 2 of the blood contained therein.

At the second phase F2, the occluding pressure is then applied and maintained for example by means of the occluding member 9 at the second region 8 of the finger/toe 2 located upstream of the first region 5. At this step, the occluding pressure P2 is preferably greater than the systolic blood pressure $P_{syst}$ to as to prevent any blood return into the distal part 3.

At the third phase F3 of the method, the draining pressure P1 is released. Since the occluding pressure P2 is greater than the systolic blood pressure $P_{syst}$, the blood volume Vs in the distal part 3 remains substantially zero.

In one preferred embodiment, the method comprises a fourth waiting phase F4 which lasts between 0 and 5 s and preferably of the order of 3 s. Advantageously this waiting period allows the guaranteed stabilization of pressures P1 and P2 before measurement.

At the fifth phase F5, the occluding pressure P2 is controllably released, for example by means of a flow restrictor 15. The occluding pressure P2 then drops continuously over the subsequent steps of the method.

Deflation is preferably linear or differential i.e. of the form $P2(t)=P_0 \cdot e^{-t/T}$. Advantageously, differential deflation allows a substantially constant measurement error to be obtained, irrespective of the occluding pressure P2 during deflation.

According to one preferred embodiment, the time needed for release of the occluding pressure P2 can be adjusted so that it takes place over a fixed number of cardiac cycles. Advantageously, this characteristic allows measurement error to be substantially constant, irrespective of the patient's heart rate.

In one preferred embodiment, the draining P1 and occluding P2 pressures are applied and released automatically, for example by means of the inflating and deflating device 10. Evidently, it is also possible for the draining pressure P1 to be applied and released manually, and for the occluding pressure P2 to be applied and released automatically.

At the sixth phase F6 of the method, at least the blood volume value at the first region 5 and at least the occluding pressure P2 at time t are acquired, for example by means of the acquisition stage 18 of the processing system 17.

The seventh phase F7 consists of detecting the possible presence of blood return to the first region 5. Blood return is characterized by filling of the finger/toe 2 with blood, and hence by a substantially positive variation in the blood volume Vs of the finger/toe 2 at the first region 5.

If there is no blood return, the eighth phase F8 consists of comparing the value of the occluding pressure P2 at time t with the minimum systolic blood pressure $P_{syst}$ which can be measured with the method, for example 10 mmHg. If the value of the occluding pressure P2 is equal to or lower than this minimum value, measurement is completed. If the value of the occluding pressure P2 is greater than this minimum value, the sixth phase F6 and following are repeated.

If blood return is detected, the value of the systolic blood pressure $P_{syst}$ is calculated at the ninth phase F9 of the method in relation to acquired data.

FIGS. 4A to 4D illustrate the calculation mode of systolic blood pressure $P_{syst}$.

Figure 4A:
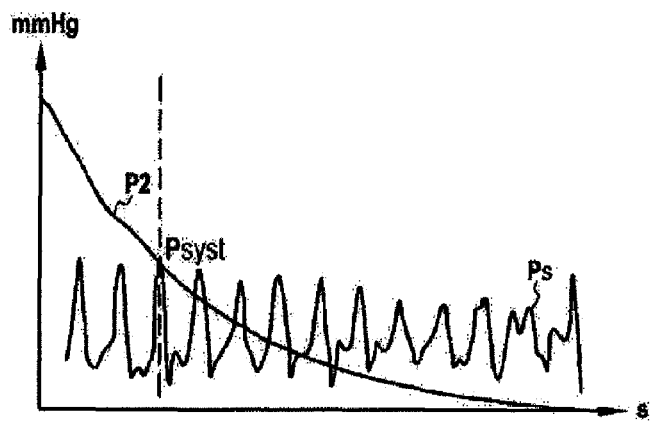
FIG. 4A is a curve giving the blood pressure and the pressure in the occluding member during deflation, as a function of time.

FIG. 4A is a curve showing a patient's arterial blood pressure Ps, expressed as mmHg, and the value of the occluding pressure P2 expressed as mmHg as a function of time.

Figure 4B:
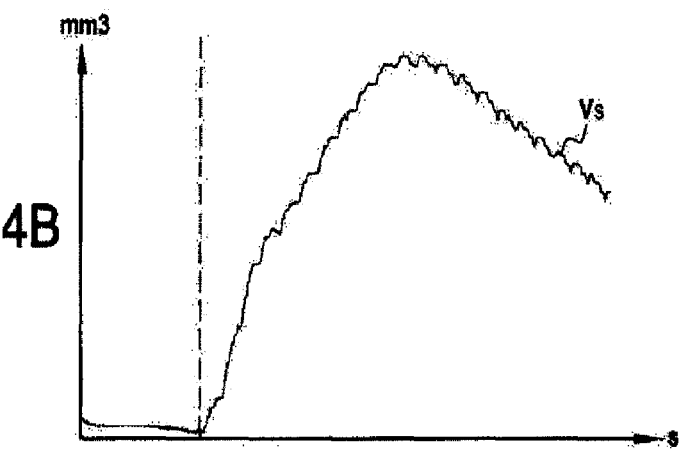
FIG. 4B is a curve giving the blood volume in the finger/toe during deflation, as a function of time.

FIG. 4B gives the value of blood volume Vs in the finger/toe 2 at the first region 5, expressed in $mm^3$ as a function of time.

For as long as the occluding pressure P2 is substantially higher than the blood pressure Ps, the blood volume Vs is substantially zero due to the drainage of the finger/toe 2 carried out prior to measurement. When the occluding pressure P2 becomes substantially equal to the blood pressure Ps, the blood returns and the blood volume Vs varies substantially positively. Blood filling necessarily starts on a systolic pulse when the pressure value Ps is highest. Therefore, the patient's systolic blood pressure $P_{syst}$ corresponds to the occluding pressure P2 at the time of blood return to the finger/toe 2.

Therefore, filling of the finger/toe 2 is due to the combined effects of pulsatile arterial flow, microcirculation and non-pulsatile arterial flow. This combination advantageously increases filling dynamics, more particularly at the start of filling, with the providing of optimum measuring precision even if the patient's blood flow is little pulsatile i.e. if blood pressures are low.

In one variant of the method, the time variation in blood volume Vs is processed for example by filtering, to extract a pulsatile component dAC therefrom and/or a non-pulsatile component dDC.

Figure 4C:
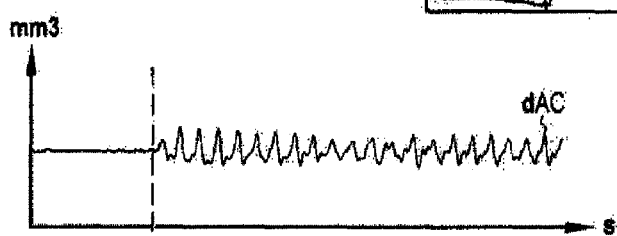
FIG. 4C is a curve showing the pulsatile component during deflation, as a function of time.

The pulsatile component dAC shown FIG. 4C and expressed in $mm^3$, represents the filling rate of the finger/toe 2 due to pulsatile arterial flow as a function of time. The pulsatile component dAC has a mean of zero with increasing and decreasing variations.

Figure 4D:
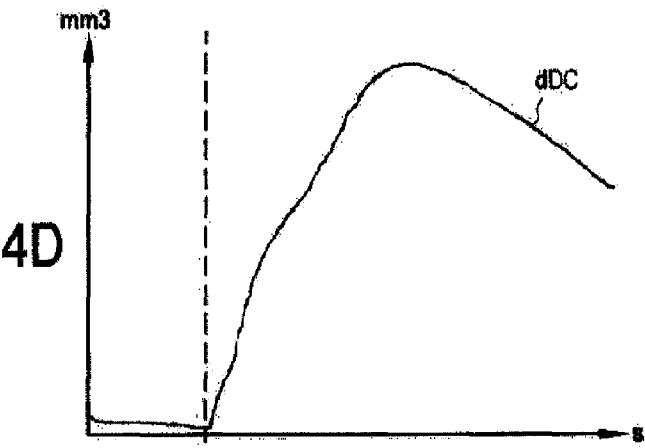
FIG. 4D is a curve giving the non-pulsatile component during deflation, as a function of time.

The non-pulsatile component dDC shown FIG. 4D and expressed in $mm^3$, illustrates filling of the finger/toe 2 resulting from pulsatile arterial flow, from microcirculation and/or from non-pulsatile arterial flow as a function of time.

The summing of the non-pulsatile component dDC and of the integral of the pulsatile component dAC substantially allows the blood volume Vs time curve to be obtained.

For as long as the occluding pressure P2 is substantially greater than the blood pressure Ps, the pulsatile dAC and non-pulsatile dDC components are substantially zero since there is no blood flow in the finger/toe 2. When the occluding pressure P2 becomes substantially equal to the blood pressure Ps, there is return of blood flow and of the pulsatile component dAC, whilst the non-pulsatile component dDC varies substantially positively.

On this account, the value of the systolic blood pressure $P_{syst}$ can be calculated from the pulsatile component dAC by determining the occluding pressure P2 at the time of re-onset of the pulsatile component dAC. This advantageously allows measurement precision to be increased by sampling with the cardiac cycle.

In addition, the value of the systolic blood pressure $P_{syst}$ can also be calculated from the non-pulsatile component dDC by determining the occluding pressure P2 at the time when the non-pulsatile component dDC varies substantially positively. This determining of the systolic blood pressure $P_{syst}$ advantageously requires lower processing dynamics than the method based on examining the time variation in blood volume.

Advantageously, the fact that a plurality of methods are provided for calculating systolic pressure $P_{syst}$ means that a polyvalent apparatus can be provided, capable of adapting to a wide range of situations.

In the illustrated example of embodiment of the measurement device 1, the ninth phase F9 for calculating systolic blood pressure $P_{syst}$ is conducted by means of the processing unit 19.

For this purpose, the processing unit 19 comprises means for determining the time when the blood volume Vs of the finger/toe 2 at the first region 5 varies substantially positively, and means for calculating the systolic blood pressure $P_{syst}$ corresponding to the occluding pressure P2 at the time when the blood volume Vs of the finger/toe 2 at the first region 5 varies substantially positively.

In one variant of embodiment, the processing unit 19 also comprises means for extracting a pulsatile component dAC representing pulsatile arterial flow in the finger/toe 2 at the first region 5 as a function of time, means for determining the time of re-onset of the pulsatile component dAC of the signal, and means for calculating the systolic blood pressure $P_{syst}$ corresponding to the occluding pressure P2 at the time of re-onset of the pulsatile component dAC of the signal.

In another variant of embodiment, the processing unit 19, for calculating the systolic blood pressure $P_{syst}$, comprises means for extracting a non-pulsatile component dDC representing filling of the finger/toe 2 resulting from pulsatile arterial flow, from microcirculation and/or from non-pulsatile arterial flow as a function of time, means for determining the time when the non-pulsatile component dDC varies substantially positively, and means for calculating the systolic blood pressure $P_{syst}$ corresponding to the occluding pressure P2 at the time when the non-pulsatile component dDC varies substantially positively.

To implement the method of the invention, the processing unit 19 also comprises comparison means between the value of the occluding pressure P2 and the value of the minimum systolic blood pressure $P_{syst}$ which can be measured by the device 1, for example 10 mmHg.

For the purpose of enabling the method of the invention to be implemented with the device 1, the control electronics 11 drive the inflating and deflating device 10 firstly to apply the draining pressure P1 before the occluding pressure P2, and secondly to release the draining pressure P1 after application of the occluding pressure P2 and before the controlled release of the occluding pressure P2.

The control electronics 11 also drive the acquisition stage 18 which, during the controlled release of the occluding pressure P2, acquires at least the data delivered by the pressure measurement system 16 and by the sensor 6.

Additionally, the control electronics 11 drive the processing unit 19 to calculate systolic pressure $P_{syst}$ during the controlled release of the occluding pressure P2 and at the time of detection of blood return in the finger/toe 2.

The invention claimed is:

1. A non-invasive method for measuring the systolic blood pressure of a digit having a distal part, the method comprising the steps of:
    applying and maintaining an astringent draining pressure greater than the systolic blood pressure of the digit on a first region located in the vicinity of the distal part of the digit, to substantially drain the digit of blood in said distal part, followed by,
    applying and maintaining an astringent occluding pressure greater than the systolic blood pressure of the digit on a second region of the digit located upstream of the first region,
    releasing the draining pressure,
    controllably releasing the occluding pressure, allowing blood to enter said drained distal region of the digit, and, at the same time, acquiring at least the occluding pressure and at least the blood volume of the digit at the first region as a function of time,
    calculating the systolic blood pressure corresponding to the occluding pressure at the time of blood return to the digit characterized by a substantially positive variation in the blood volume of the digit at the first region;
    wherein the systolic blood pressure is measured only during deflation.

2. The method according to claim 1, wherein the draining pressure is greater than the systolic blood pressure of the digit.

3. The method according to claim 1, wherein the draining and occlusion pressures are applied and released automatically.

4. The method according to claim 1, wherein the draining pressure is applied and released manually, and the occluding pressure is applied and released automatically.

5. The method according to claim 1, further comprising a waiting phase which lasts between 0 and 5 s, wherein the waiting phase occurs after release of the draining pressure.

6. The method according to claim 1, wherein the step for calculating the systolic blood pressure comprises:
    extracting a pulsatile component representing the pulsatile arterial flow in the digit, from the variation in blood volume of the digit at the first region as a function of time,
    calculating the systolic blood pressure by determining the occluding pressure at the time of re-onset of the pulsatile component of the signal.

7. The method for measuring blood pressure according to claim 1, wherein the step for calculating systolic blood pressure comprises:
    extracting a non-pulsatile component representing filling of the digit resulting from pulsatile arterial flow, from microcirculation and/or from non-pulsatile arterial flow, using the variation in blood volume of the digit at the first region as a function of time,
    calculating systolic blood pressure by determining the occluding pressure at the time when the non-pulsatile component varies substantially positively.

8. The method according to claim 1, comprising adjusting the time needed for release of the occluding pressure so that release of the occluding pressure takes place over a fixed number of cardiac cycles.

9. A non-invasive device for measuring the systolic blood pressure of a digit having a distal part, the device comprising:
    a first element comprising a sensor configured to measure the blood volume of a digit at a first region located in the vicinity of the distal part of the digit, and a draining member configured to apply or transmit a draining pressure, that is greater than the systolic blood pressure of the digit, to the first region of the digit, and to substantially drain the digit of blood in said distal part,
    a second element comprising an arterial occluding member configured to apply and/or maintain an occluding pressure on a second region of the digit located upstream of the first region, to allow blood to enter the drained distal part of the digit, and a servo-controlled inflating and deflating device controlled by control electronics and ensuring the inflation and deflation of at least the arterial occluding member, a pressure measurement system measuring at least the pressure applied by the arterial occluding member, and a processing system controlled by the control electronics and comprising:

an acquisition stage which acquires at least the data delivered by the pressure measurement system (16) and by the sensor, a processing unit comprising:

means for determining the time when the blood volume of the digit at the first region varies substantially positively, means for calculating systolic blood pressure corresponding to the occluding pressure at the time when the blood volume in the digit at the first region varies substantially positively;

wherein the device is configured to measure the systolic blood pressure only during deflation.

10. The device according to claim 9, wherein the inflating and deflating device also ensures the inflation and deflation of the draining member.

11. The device according to claim 9, wherein at least the occluding member is formed of an air chamber.

12. The device according to claim 9, wherein the processing unit further comprises:

means for extracting a pulsatile component representing the pulsatile arterial flow in the digit (2) at the first region as a function of time, means for determining the time of re-onset of the pulsatile component of the signal, means for calculating the systolic blood pressure corresponding to the occluding pressure at the time of re-onset of the pulsatile component of the signal.

13. The device according to claim 9, wherein the processing unit further comprises:

means for extracting a non-pulsatile component representing filling of the digit resulting from pulsatile arterial flow, from microcirculation and/or from non-pulsatile arterial flow, as a function of time, means for determining the time when the non-pulsatile component varies substantially positively, means for calculating the systolic blood pressure corresponding to the occluding pressure at the time when the non-pulsatile component varies substantially positively.

14. The device according to claim 9, wherein the processing unit comprises comparison means between the value of the occluding pressure and a minimum value of the systolic blood pressure measured by the device.

15. The device according to claim 9, wherein the control electronics drive:

the inflating and deflating device to apply the draining pressure before application of the occluding pressure, the inflating and deflating device, to release the draining pressure after application of the occluding pressure and before the controlled release of the occluding pressure, the acquisition stage to acquire, during the controlled release of the occluding pressure, at least the data delivered by the pressure measurement system and by the sensor, the processing unit to calculate the systolic pressure during the controlled release of the occluding pressure and at the time of detection of blood return into the digit.

16. The method according to claim 5, wherein the waiting phase lasts in the order of 3 seconds.

17. The method according to claim 1, wherein the astringent occluding pressure is applied and maintained at a pressure greater than 30 mmHg.

18. The method according to claim 5, wherein a minimum value of the systolic blood pressure measured is 10 mmHg.

* * * * *